United States Patent
Wickham et al.

(10) Patent No.: US 11,284,928 B2
(45) Date of Patent: Mar. 29, 2022

(54) SURGICAL IMPLANT AND METHOD OF USE

(71) Applicant: Warsaw Orthopedic, Inc., Warsaw, IN (US)

(72) Inventors: Jeffrey N. Wickham, Ooltewah, TN (US); Mark C. Dace, Collierville, TN (US); Alexander Vaccaro, Gladwyne, PA (US); Brian A. O'Shaughnessy, Nashville, TN (US); Andrew C. Hecht, New York, NY (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 26 days.

(21) Appl. No.: 16/222,627

(22) Filed: Dec. 17, 2018

(65) Prior Publication Data

US 2020/0188002 A1 Jun. 18, 2020

(51) Int. Cl.
*A61B 17/86* (2006.01)
*A61B 17/70* (2006.01)

(52) U.S. Cl.
CPC ...... *A61B 17/8625* (2013.01); *A61B 17/7001* (2013.01)

(58) Field of Classification Search
CPC .............. A61B 17/8625; A61B 17/863; A61B 17/8635
See application file for complete search history.

(56) References Cited

U.S. PATENT DOCUMENTS

| | | | |
|---|---|---|---|
| 5,019,079 A | 5/1991 | Ross | |
| 5,743,914 A | 4/1998 | Skiba | |
| D411,009 S | 6/1999 | Asfora | |
| 6,280,442 B1 * | 8/2001 | Barker | A61B 17/7037 606/256 |
| 7,044,953 B2 | 5/2006 | Capanni | |
| 8,002,811 B2 * | 8/2011 | Corradi | A61B 17/862 606/300 |
| 8,808,338 B2 | 8/2014 | Martin | |
| 9,161,745 B2 | 10/2015 | Dodson | |
| 9,295,488 B2 | 5/2016 | Asfora | |
| 9,561,055 B1 | 2/2017 | Karim | |
| 10,085,776 B2 | 10/2018 | Blain | |
| D834,194 S | 11/2018 | Blain et al. | |
| 10,188,429 B2 | 1/2019 | Carlson et al. | |
| 10,194,955 B2 | 2/2019 | Blain et al. | |

(Continued)

OTHER PUBLICATIONS

International Search Report—PCT/US2019/056474 ISA/KR International Application Division, Written Opinion of the International Searching Authority Korean Intellectual Property Office, 1 89 Cheongsa-ro, Seo-gu, Daejeon, 35208, Republic of Korea, dated Feb. 6, 2020.

*Primary Examiner* — Tessa M Matthews

(74) *Attorney, Agent, or Firm* — Sorell, Lenna & Schmidt, LLP

(57) ABSTRACT

A bone screw has a first portion including a head. A second portion includes a threaded shaft having a length and a major diameter. The shaft includes a length-to-major diameter ratio of less than about 2.0. The thread has a minor diameter and includes a major-diameter-to-minor diameter ratio of greater than about 2.0. The shaft further has at least one thread including a pitch of greater than about 1.0 mm and defining a pitch cavity for disposal of tissue. Systems and methods of use are disclosed.

17 Claims, 6 Drawing Sheets

(56) References Cited

U.S. PATENT DOCUMENTS

| | | |
|---|---|---|
| 10,307,186 B2 | 6/2019 | Schafer et al. |
| 2003/0045881 A1* | 3/2003 | Barouk ................ A61B 17/863 606/304 |
| 2003/0078581 A1 | 4/2003 | Frei |
| 2004/0044345 A1* | 3/2004 | DeMoss ............. A61B 17/8625 606/916 |
| 2007/0250063 A1 | 10/2007 | Vlahos |
| 2008/0221583 A1 | 9/2008 | Sharifi-Mehr et al. |
| 2009/0018589 A1 | 1/2009 | Smisson, III et al. |
| 2011/0245875 A1 | 10/2011 | Karim |
| 2012/0071927 A1 | 3/2012 | Beger et al. |
| 2012/0143266 A1* | 6/2012 | Jackson ............. A61B 17/7037 606/328 |
| 2015/0265316 A1 | 9/2015 | Schwab |
| 2015/0289906 A1 | 10/2015 | Murray et al. |
| 2015/0313658 A1 | 11/2015 | Kolb |
| 2016/0166288 A1* | 6/2016 | Biedermann ...... A61B 17/7037 606/266 |
| 2016/0361096 A1* | 12/2016 | van der Pol ....... A61B 17/7076 |
| 2018/0177533 A1 | 6/2018 | Jones et al. |
| 2018/0289397 A1* | 10/2018 | Buttermann ....... A61B 17/7038 |
| 2018/0368889 A1* | 12/2018 | Cole ................. A61B 17/7032 |
| 2020/0093525 A1* | 3/2020 | Zastrozna ............ A61B 17/863 |
| 2020/0096035 A1* | 3/2020 | Houck ............... F16B 25/0047 |
| 2020/0121365 A1* | 4/2020 | Biester ................ A61B 17/686 |
| 2020/0367952 A1* | 11/2020 | Ramsay ............... A61B 17/864 |

\* cited by examiner

| L/D RATIO | SCREW DIAMETER | | | | | |
|---|---|---|---|---|---|---|
| | 4.5 | 5 | 5.5 | 6 | 6.5 | 7 |
| SCREW LENGTH 7 | 1.6 | 1.4 | 1.3 | 1.2 | 1.1 | 1.0 |
| SCREW LENGTH 8 | 1.8 | 1.6 | 1.5 | 1.3 | 1.2 | 1.1 |
| SCREW LENGTH 9 | 2.0 | 1.8 | 1.6 | 1.5 | 1.4 | 1.3 |
| SCREW LENGTH 10 | 2.2 | 2.0 | 1.8 | 1.7 | 1.5 | 1.4 |
| SCREW LENGTH 11 | 2.4 | 2.2 | 2.0 | 1.8 | 1.7 | 1.6 |

SURGICAL IMPLANT AND METHOD OF USE

TECHNICAL FIELD

The present disclosure generally relates to medical devices for the treatment of spinal disorders, and more particularly to a surgical implant system including a bone fastener and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, implants such as bone fasteners, plates, connectors and vertebral rods are often used to provide stability to a treated region. These implants can redirect stresses away from a damaged or defective region while healing takes place to restore proper alignment and generally support the vertebral members. For example, the plates, connectors and/or rods may be attached via the fasteners to the exterior of one or more vertebral members. This disclosure describes an improvement over these prior technologies.

SUMMARY

In one embodiment, a spinal implant for use with a surgical treatment is provided. The spinal implant includes a bone screw having a first portion including a head. A second portion includes a threaded shaft having a length and a major diameter. The shaft includes a length-to-major diameter ratio of less than about 2.0. The thread has a minor diameter and includes a major-diameter-to-minor diameter ratio of greater than about 2.0. The shaft further has at least one thread including a pitch of greater than about 1.0 mm and defining a pitch cavity for disposal of tissue. In some embodiments, systems and methods are disclosed.

In one embodiment, the bone screw includes a first portion having a head. A second portion connected to the first portion and includes a threaded shaft having a length and a major diameter, the shaft including a length-to-major diameter ratio of less than about 2.0. The thread has a minor diameter including a major-diameter-to-minor-diameter ratio of greater than about 2.0. The shaft further has at least one thread including a pitch of greater than about 1.0 mm, a thread depth, a base and a tip of about 1.5 mm. A thread-depth-to-base ratio is about 5. The at least one thread includes a leading surface of a flank and a trailing surface of an adjacent flank, the leading surface and the trailing surface defining a pitch cavity therebetween.

In one embodiment, a method for treating a spine is disclosed. The method comprising the steps of: delivering a bone screw along a straight-in trajectory to a surgical site including vertebral tissue, the bone screw comprising a first portion including a head, and a second portion including a threaded shaft having a length and a diameter with a length-to-diameter ratio of less than about 2.0, the shaft having a major diameter and a minor diameter including a major-diameter-to-minor diameter ratio of greater than about 2.0, the shaft further having at least one thread including a pitch of greater than about 1.0 mm and defining a pitch cavity; and engaging the bone screw along the straight-in trajectory with the vertebral tissue to connect the bone screw with the vertebral tissue and dispose vertebral tissue with the pitch cavity.

BRIEF DESCRIPTION OF THE DRAWINGS

The present disclosure will become more readily apparent from the specific description accompanied by the following drawings, in which:

FIG. 7 shows a table of dimensions of components of one embodiment of a system in accordance with the principles of the present disclosure;

DETAILED DESCRIPTION

Figure 1:
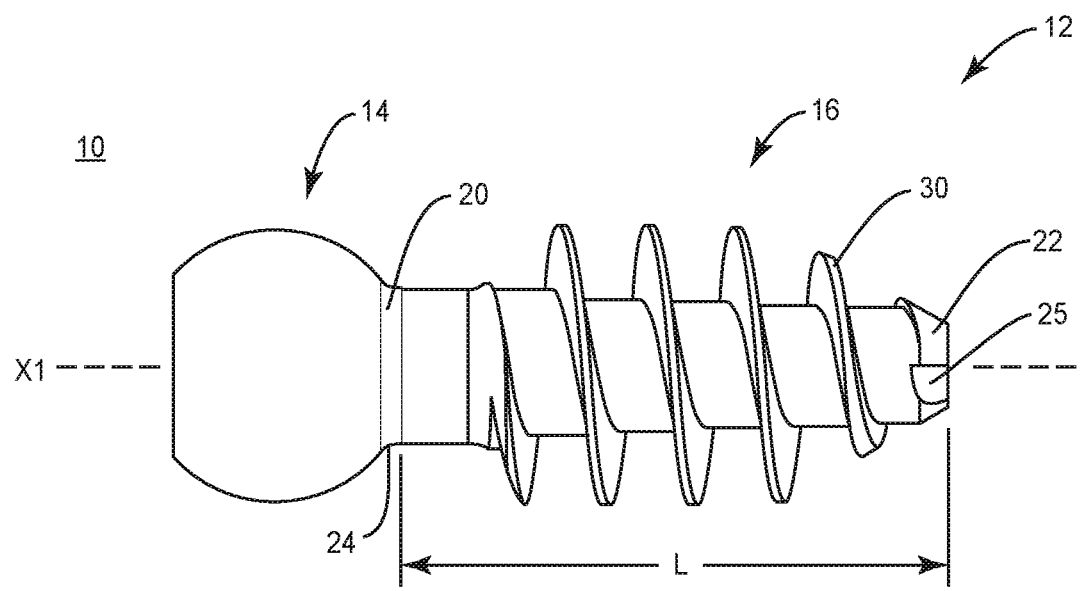
FIG. 1 is a side view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone screw and a method for treating a spine.

In some embodiments, the present surgical system includes a spinal implant comprising a bone screw having a selected length and a selected diameter. In some embodiments, the spinal implant is configured for a minimally invasive lateral mass screw placement, which may include cervical lateral mass screw placement and/or upper thoracic rib-head screw placement. In some embodiments, the spinal implant includes a bone screw configured to reduce a risk of vertebral artery or nerve root injury. In some embodiments, the spinal implant includes a bone screw having a selected length and a selected diameter to facilitate lateral mass placement. In some embodiments, the spinal implant includes a bone screw having a length to diameter aspect ratio in a range of about 2.0 or less, a diameter in a range of about 4.5 millimeters (mm) to about 8.0 mm and a length in a range of about 5.0 mm to about 10.0 mm. In some embodiments, the spinal implant includes a bone screw having a diameter in a range of about 5.5 mm to about 7.0 mm and a length in a range of about 8.0 mm to about 9.0 mm.

In some embodiments, the present surgical system includes a spinal implant comprising a bone screw that is employed with a surgical method that aligns the bone screw with a direction of a force application to maximize the pullout force from a trajectory standpoint. In some embodiments, maximizing pullout increases the solidity of the construct. This facilitates a solid structure when engaged with small bone anatomy, for example, C7 of the vertebrae or with bone having poor quality. This alignment of bone screw 12 with the direction of the pullout force increases the holding power of the screw. In some embodiments, the surgical method includes a step of aligning a bone screw along a straight-in screw trajectory and/or surgical pathway. In some embodiments, the bone screw includes an axis aligned with a direction of pullout force to provide an increased resistance to pullout. In some embodiments, the bone screw is configured with a shortened length to resist and/or prevent vertebral artery or nerve root injury. In some embodiments, the shortened bone screw is configured to take advantage of the straight-in trajectory.

In some embodiments, the present surgical system includes a spinal implant comprising a bone screw that is employed with a surgical method, such as, for example, a Roy-Camille technique to resist and/or prevent vertebral artery or nerve root injury. In some embodiments, the present surgical system includes a spinal implant comprising a bone screw that is employed with a surgical method to facilitate a safe, simple, secure fixation and less invasive procedure for lateral mass screw placement. In some embodiments, the present surgical system includes a spinal implant comprising a bone screw that is employed with a surgical method to prevent a breach of an anterior cortex of a lateral mass.

In some embodiments, the present surgical system includes a bone screw configured with a selected diameter and a selected bone screw length to provide an increased pullout force. In some embodiments, the selected diameter is based on a size of a lateral mass. In some embodiments, the bone screw can have a diameter in a range of about 5.0 mm to about 7.0 mm to maintain bone for good structural integrity.

In some embodiments, the bone screw has a tapered minor diameter. In some embodiments, the bone screw has a length of about 9.0 mm. In some embodiments, the bone screw has a diameter of about 5.5 mm. In some embodiments, the bone screw has a tapered tip. In some embodiments, the bone screw has a thread cutting element.

In some embodiments, the present surgical system includes a spinal implant comprising a bone screw having a selected diameter that is employed with a surgical method to facilitate cervical procedures. In some embodiments, the present surgical system includes a spinal implant comprising a bone screw having a length to diameter ratio in a range of about 2.0 or less. In some embodiments, the bone screw has a diameter in a range of about 4.5 mm to about 8.0 mm and a length in a range of about 5.0 mm to about 10.0 mm. In some embodiments, the bone screw has a length in a range of about 5.5 mm to about 7.0 mm and/or a diameter in a range of about 6.0 mm to about 8.0 mm.

In some embodiments, the bone screw includes a cervical lateral mass screw designed for a straight-in trajectory. In some embodiments, the bone screw is configured for use with a posterior cervical fusion system and is simple, safe, secure and minimizes morbidity. In some embodiments, the bone screw is configured for a straight-in trajectory in the C3-C7 lateral masses. In some embodiments, the bone screw is configured to reduce and/or prevent any risk to the vertebral artery, nerve roots, and lateral wall, and is also safe for the facet joints. In some embodiments, the bone screw is configured to improve ease and speed of placement of the bone screw. In some embodiments, the bone screw is configured to provide an increase in pullout strength. In some embodiments, the bone screw is configured for a straight-in trajectory to facilitate minimally invasive cervical procedures, such as, for example, an anterior cervical discectomy and/or fusion procedures.

In some embodiments, the bone screw includes a thread having an increased diameter relative to a screw shank. In some embodiments, the thread includes a moderate pitch. In some embodiments, the bone screw includes a thread major diameter that is 2 times greater than the thread minor diameter. In some embodiments, the thread pitch is about 1.5 mm. In some embodiments, this configuration facilitates threads disrupting, scraping, cutting, removing and/or slicing tissue and/or bone for disposal of bone between the threads, thus improving the holding power. In some embodiments, the bone screw includes a thread having a decreased width at the base relative to the thread height to facilitate disrupting, scraping, cutting, removing and/or slicing tissue and/or bone. In some embodiments, the bone screw includes a thread having a thin tip.

In some embodiments, the bone screw includes a height that is about 5 times a width of a base. In some embodiments, the bone screw includes a tip having a width of about 0.15 mm. In some embodiments, the bone screw includes dimensions, as described herein, in a configuration such that the bone screw threads cut and/or slice through bone like a narrow wedge. In some embodiments, the bone screw configuration and dimensions, as described herein, minimizes impact to the microstructure of tissue. In some embodiments, the bone screw is configured to allow the tissue and/or bone to contract against surfaces of the bone screw thread creating friction and providing tactile feedback to a practitioner.

In some embodiments, the bone screw includes a flat tip. In some embodiments, the flat tip is configured to resist and/or prevent damage to the cortical wall on the anterior side of the vertebra. In some embodiments, the flat tip causes the screw to strip the hole rather than go through the cortical bone. In some embodiments, the flat tip is configured to resist and/or prevent bone breaching when the lateral mass is not thick enough to fully accommodate an approximately 9.0 mm screw.

In some embodiments, the bone screw is utilized with a surgical navigation system. In some embodiments, the bone screw is configured for minimally invasive cervical surgery as the bone screw can be inserted in a straight-in trajectory. In some embodiments, the straight-in trajectory facilitates insertion of the bone screw as there is less tissue that the surgeon must navigate through.

In some embodiments, the bone screw includes a length and diameter aspect ratio. In some embodiments, the bone screw includes a length of about 8 mm or less and with a diameter less than the length. In some embodiments, the bone screw includes a length of about 8 mm and a diameter of about 5.5 mm. In some embodiments, the bone screw includes a navigation component configured to facilitate minimally invasive procedures.

In some embodiments, the bone screw includes a thread having a leading edge extending relative to an axis of the bone screw and defines a leading edge angle. In some embodiments, the bone screw includes a thread having a trailing edge extending relative to an axis of the bone screw and defines a trailing edge angle. In some embodiments, the thread includes a thread tip. In some embodiments, the thread tip includes a width of about 0.15 mm. In some embodiments, the leading edge angle is about 5 degrees. In some embodiments, the trailing edge angle is about 5 degrees. In some embodiments, the thread includes a height of about 1.3 mm.

In some embodiments, the thread tip includes a width in a range of about 0.075 mm to about 0.400 mm. In some embodiments, the leading edge angle is in a range of about −4 degrees to about 15 degrees. In some embodiments, the trailing edge angle is in a range of about 4 degrees to about 15 degrees. In some embodiments, the thread height is in a range of about 0.75 mm to about 3.5 mm.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of a surgical system including one or more spinal implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7, there are illustrated components of a surgical system 10 including a spinal implant, such as, for example, a bone screw 12.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Bone screw 12 includes a first portion, such as, for example, a head 14 and a second portion, such as, for example a shaft 16. Head 14 includes a substantially spherical portion. Head 14 includes a tool-engaging portion 18 configured to engage a surgical tool or instrument (not shown), as described herein. In some embodiments, portion 18 includes a hexagonal cross-section to facilitate engagement with a surgical tool or instrument. In some embodiments, head 14 may have alternative cross-sections, such as, for example, rectangular, polygonal, hexalobe, oval, or irregular. In some embodiments, portion 18 may have a cruciform, phillips, square, polygonal or star cross sectional configuration for disposal of a correspondingly shaped portion of a surgical tool or instrument.

Figure 9:
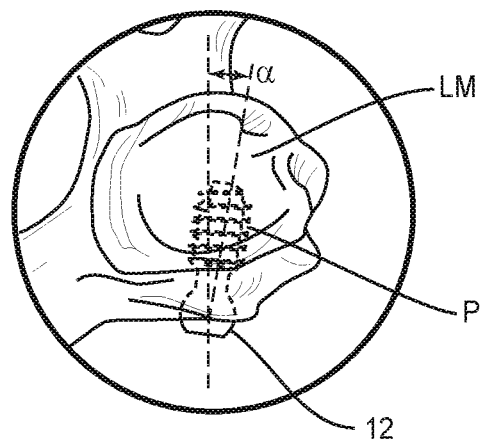
FIG. 9 is an enlarged view of section B shown in FIG. 8 in connection with components of one embodiment of a system in accordance with the principles of the present disclosure.

Shaft 16 extends along an axis X1. Shaft 16 includes an end 20 and an end 22. End 20 forms a section, such as, for example, a neck 24 with head 14. Neck 24 is disposed adjacent head 14. End 22 is configured for engagement with tissue, such as, for example, lateral mass tissue LM, as shown and described with regard to FIGS. 8-11. In some embodiments, shaft 16 is configured for disposal along a surgical pathway P, as shown in FIGS. 9 and 11, oriented at an angle α. In some embodiments, angle α is in a range of −5 through 15 degrees, and in some embodiments 0 through 10 degrees, relative to a direct posterior surgical approach, as described herein. In some embodiments, end 22 includes a tapered tip. In some embodiments, end 22 includes a blunt tip configured to facilitate resistance and/or prevent damage to surrounding tissue and/or nerves. In some embodiments, the blunt tip configuration can be employed to optimize bone purchase. In some embodiments, end 22 includes a thread cutting element, such as, for example, a groove 25 configured to facilitate engagement with tissue. In some embodiments, groove 25 is configured to penetrate tissue to facilitate engagement of a thread 30 with tissue, as described herein.

Shaft 16 includes a shaft length L and an outer surface 26. Surface 26 includes an external thread 30. Thread 30 extends along a portion of shaft 16 between end 20 and end 22, as shown in FIG. 1. In one embodiment, thread 30 is continuous along surface 26. In one embodiment, thread 30 may include a single thread turn or a plurality of discrete threads. In some embodiments, other penetrating elements may be located on shaft 16, such as, for example, a nail configuration, barbs, expanding elements, raised elements, ribs, and/or spikes to facilitate engagement of shaft 16 with tissue. In some embodiments, thread 30 may be self-tapping or intermittent. In some embodiments, shaft 16 includes a tapered portion.

Figure 3:
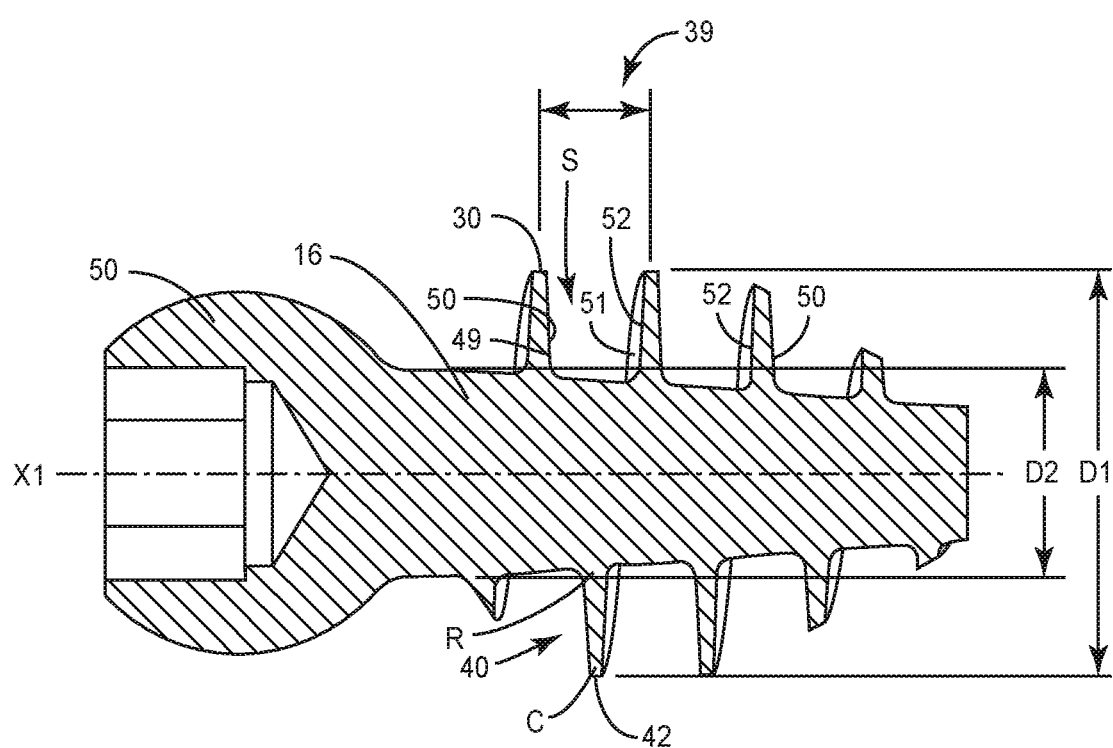
FIG. 3 is a cross section view of the components shown in FIG. 1.

Thread 30 includes a major diameter D1, as shown in FIG. 3. In some embodiments, bone screw 12 has a selected shaft length L and a selected major diameter D1. In some embodiments, a shaft length L to major diameter D1 aspect ratio is less than about 2.0. In some embodiments, bone screw 12 has a selected shaft length L and a selected major diameter D1 employed with a minimally invasive lateral mass screw placement to reduce a risk of vertebral artery or nerve root injury. In some embodiments, shaft 16 includes a minor diameter D2. In some embodiments, a ratio of major diameter D1 to minor diameter D2 is greater than about 2.0. Thread 30 includes a pitch 39 of about 1.5 mm.

Thread 30 has a flank 40 extending between a base R and a crest C. Flank 40 includes a depth having a height H1. In some embodiments, height H1 is in a range of about 0.75 mm to about 3.50 mm. Flank 40 extends from base R having a width W1. In some embodiments, width W1 is about 0.3 mm. In some embodiments, a ratio of height H1 to width W1 is at least 5.0.

Crest C includes a tip 42 having a width W2. In some embodiments, width W2 is in a range of about 0.075 to about 0.400. In some embodiments, width W2 is about 0.150 mm. In some embodiments, height H1, width W1 and width W2 are configured to facilitate thread 30 disrupting, scraping, cutting, removing and/or slicing tissue and/or bone, for example, having a narrow wedge configuration. In some embodiments, height H1, width W1 and width W2 are configured to minimize an impact to tissue and/or bone microstructure. In some embodiments, height H1, width W1 and width W2 are configured to allow the tissue and/or bone to contract against surfaces of thread 30 creating friction and providing tactile feedback to a practitioner.

Figure 6:
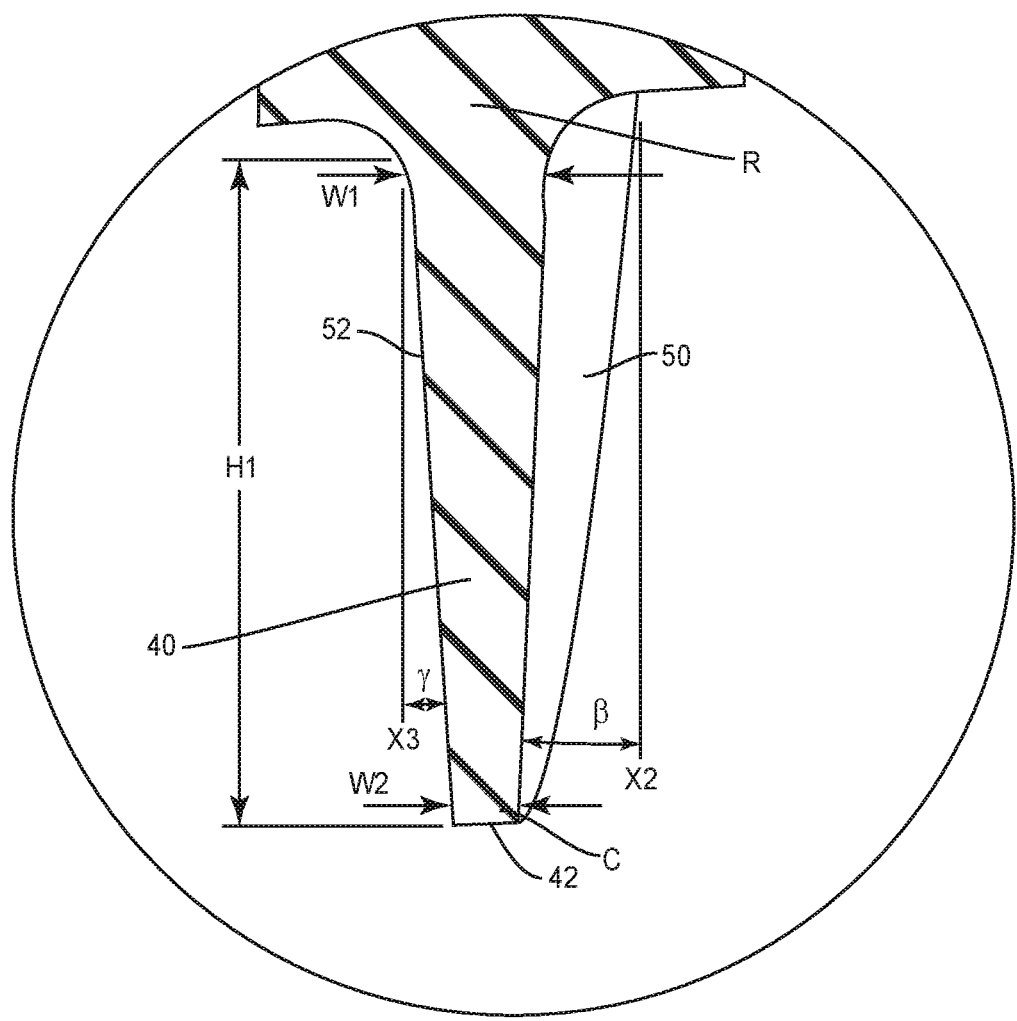
FIG. 6 is a break away view of section A shown in FIG. 5.
Figure 8:
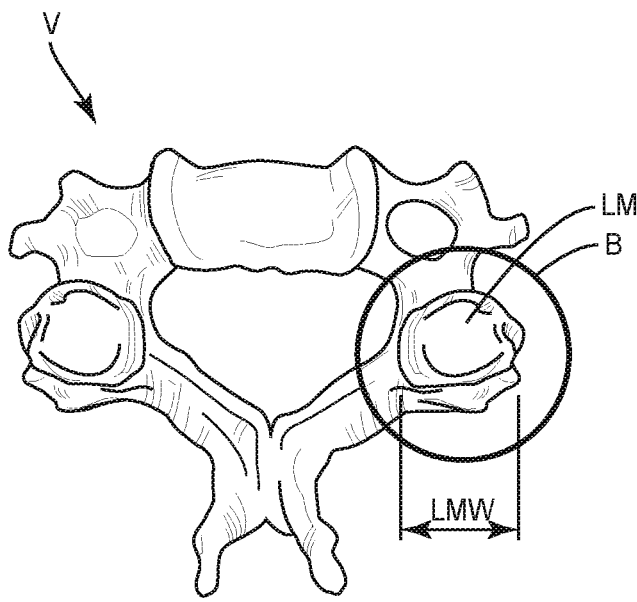
FIG. 8 is an axial view, and more particularly a caudal view, of vertebrae.

Flank 40 includes a surface 49 that defines a leading edge 50 and a surface 51 that defines a trailing or lagging edge 52. Leading edge 50 defines an angle β relative to an axis X2. Axis X2 is disposed transverse, such as for example orthogonal to axis X1, as shown in FIG. 6. In some embodiments, angle β is in a range of about −4.0 degrees to about 15.0 degrees. In some embodiments, angle β is about 5.0 degrees.

Trailing edge 52 defines an angle γ relative to an axis X3. Axis X3 is disposed transverse, such as for example orthogonal to axis X1, as shown in FIG. 6. In some embodiments, angle γ is in a range of about −4.0 degrees to about 15.0 degrees. In some embodiments, angle γ is about 5.0 degrees.

Figure 2:
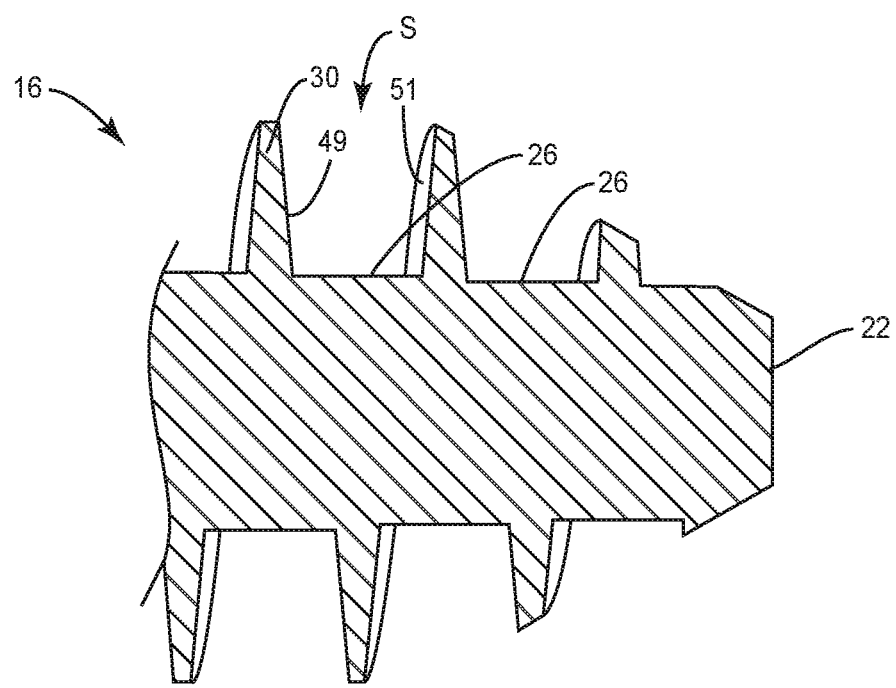
FIG. 2 is a break away cross section view of components of the system shown in FIG. 1.

Surface 49, a portion of surface 26 and surface 51 of an adjacent flank 40 define a pitch cavity S, as shown in FIGS. 2 and 3. Surfaces 49, 26, 51 are relatively oriented and/or configured for disposal of vertebral tissue with cavity S, which may include agents or biologics, as described herein. In some embodiments, surfaces 49, 26, 51 are relatively oriented and/or configured to gather vertebral tissue for disposal with cavity S. Such tissue, agent and/or biologics can be disposed and/or imbedded with cavity S to promote bone growth to enhance fusion of bone screw 12 with vertebral tissue and to provide an increased resistance and pullout force of bone screw 12.

Cavity S can be dimensioned by the ratio of diameter D1 to diameter D2, and pitch 39 to facilitate bone growth and/or fixation with tissue. For example, cavity S includes a depth equal to height H1 of flank 40. Cavity S includes a width equal to pitch 39 of thread 30 less a width of one of threads 30. Cavity S is configured to receive cut and/or disrupted tissue for disposal therein to promote bone growth to enhance fusion of bone screw 12 with vertebral tissue and to provide an increased resistance and pullout force of bone screw 12. As thread 30 engages tissue, the surfaces of thread 30 disrupt, scrape, cut and/or remove tissue and guide the cut tissue into cavity S. In some embodiments, surfaces 49, 26, 51 are relatively oriented and/or configured for disposal of vertebral tissue to facilitate bone through-growth to provide for an improved bone attachment to bone screw 12 for engagement with cortical bone and cancellous bone within vertebrae.

In some embodiments, thread form 30 defines a plurality of spaced apart cavities S. In some embodiments, cavities S may be variously positioned, for example, evenly spaced around at least a portion of shaft 16. In some embodiments, external grating materials or biologics may be prepacked with bone screw 12. In some embodiments, surface 49 and/or surface 51 includes at least one tissue gathering member. In some embodiments, the tissue gathering member may include a cutting edge. In some embodiments, the cutting edge may include a rasp-like configuration. In some embodiments, the cutting edge is configured to engage tissue, such as, for example, cortical bone and/or cancellous bone, such as, to cut, shave, shear, incise and/or disrupt such tissue. In some embodiments, all or a portion of the cutting edge may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, the cutting edge may be rough, textured, porous, semi-porous, dimpled, knurled, toothed, grooved and/or polished to facilitate engagement and cutting of tissue. In some embodiments, the cutting edge forms a tunnel configured to guide, drive and/or direct the cut tissue into cavity S to facilitate fusion of bone screw 12 with tissue, such as, for example, vertebrae.

Edges 50, 52 are configured to guide, drive and/or direct the cut tissue into cavity S to facilitate fusion of bone screw 12 with tissue, such as, for example, vertebrae. Manipulation of bone screw 12, including rotation and/or translation, causes edges 50, 52 to disrupt, scrape, cut and/or remove tissue at a surgical site and guide the cut tissue into cavity S. The tissue becomes imbedded into cavity S to promote bone growth to enhance fusion of bone screw 12.

In some embodiments, the dimensions of bone screw 12, as described herein, are configured to facilitate thread 30 cutting and/or slicing through bone like a narrow wedge. In some embodiments, the dimensions of bone screw 12 are configured to minimize an impact to the microstructure of tissue. In some embodiments, the dimensions of bone screw 12 are configured to allow the tissue and/or bone to contract against surfaces of thread 30 creating friction and providing tactile feedback to a practitioner.

In some embodiments, surgical system 10 can include one or a plurality of spinal implants, such as, for example, bone screws 12 provided in a kit or as a set having various configurations and dimensions. In some embodiments, the kit or set of bone screws 12 can be provided in various sizes from which a desired bone screw size and/or shape can be selected by a surgeon and/or selected for implant based on pre-operative planning or conditions encountered during surgery, as described herein.

In some embodiments, bone screw 12 is employed with a surgical method that aligns bone screw 12 with a direction of a force application to maximize a pullout force from along a trajectory of surgical pathway P to resist and/or prevent vertebral artery or nerve root injury. In some embodiments, bone screw 12 is aligned along a straight-in screw trajectory of surgical pathway P. A straight-in trajectory is oriented such that the trajectory is aligned perpendicular to the lateral mass. The tip of bone screw 12 is angled about 0 degrees cranially, and about 0 degrees to about 10 degrees laterally with respect to a surface of the lateral mass. For example, when a patient bends in flexion, the natural motion of the vertebrae would be to curve forward away from the rod. The spinal rods and bone screws 12 are implanted to maintain the vertebrae in position, preventing forward motion. A direction of force is about perpendicular to the rod. Disposal of bone screw 12 straight-in, axially aligns bone screw 12 with the force working to pull the screw back out. This alignment of bone screw 12 with the direction of the pullout force increases the holding power of the screw.

In some embodiments, axis X1 of bone screw 12 is aligned with a direction of pullout force to provide an increased resistance to pullout. In some embodiments, bone screw 12 is employed with a cervical surgical procedure, such as, for example, a Roy-Camille technique. In some embodiments, bone screw 12 reduces a risk of vertebral artery and/or nerve root injury due to length L being configured to avoid breaching an anterior cortex of lateral mass tissue LM.

Figure 10:
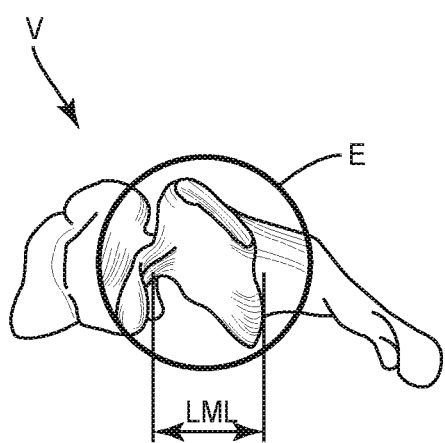
FIG. 10 is a side view of the vertebrae of FIG. 8.
Figure 11:
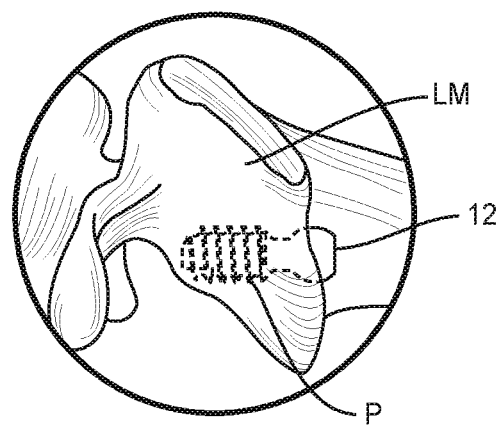
FIG. 11 is an enlarged view of section E shown in FIG. 10 in connection with components of one embodiment of a system in accordance with the principles of the present disclosure.

In some embodiments, bone screw 12 is configured with a selected length L based on a lateral mass length LML of a vertebral level of a cervical spine, as called out in FIG. 10. In some embodiments, bone screw 12 includes selected length L in a range of about 5.0 mm to about 10.0 mm. In some embodiments, selected length L is in a range of about 5.5 mm to about 7.0 mm.

In some embodiments, diameter D1 is selected based on a lateral mass width LMW of a vertebral level of a cervical spine to maximize diameter D1 while maintaining the structural integrity of bone screw 12 when engaged with lateral mass tissue LM. A maximum diameter D1 and shaft length L are selected to provide an increased pullout force. In some embodiments, selected diameter D1 is in a range of about 4.5 mm to about 8.0 mm. In some embodiments, selected diameter D1 is in a range of about 6.0 mm to about 8.0 mm.

In some embodiments, as shown by the table in FIG. 6, selected length L and selected diameter D1 have a ratio L/D1 of bone screw 12 that is about 2.0 or less. For example, bone screw 12 includes length L in a range of about 5.0 mm to about 10.0 mm and diameter D1 in a range of about 4.5 mm to about 8.0 mm such that ratio L/D1 of bone screw 12 is about 2.0 or less. In some embodiments, bone screw 12 includes length L in a range of about 6.0 mm to about 8.0 mm and diameter D1 in a range of about 5.5 mm to about 7.0 mm such that ratio L/D1 of bone screw 12 is in a range of about 0.9 to about 1.5. In some embodiments, diameter D1 and/or length L are selected to provide a ratio L/D1 such that bone screw 12 resists and/or prevents damage to a vertebral artery and nerve roots while maintaining the structural integrity of bone screw 12. In some embodiments, ratio L/D1 is less than about 2.0.

In some embodiments, length L of bone screw 12 is determined based on a patient anatomy, such as, for example, cervical lateral mass length LML and cervical lateral mass width LMW at a cervical level, such as, for example, between cervical levels C3-C7. In some cases, the lateral mass length LML and the lateral mass width LMW vary between male and female patients.

For example, a male patient anatomy can have a cervical lateral mass length of about 11.7 mm and a cervical lateral mass width of about 11.1 mm for a sub-axial cervical spine at cervical level C3. In some examples, a male patient anatomy can have a cervical lateral mass length of about 12.6 mm and a cervical lateral mass width of about 11.4 mm for a sub-axial cervical spine at cervical level C4. In some examples, a male patient anatomy can have a cervical lateral mass length of about 12.9 mm and a cervical lateral mass width of about 12.4 mm for a sub-axial cervical spine at cervical level C5. In some examples, a male patient anatomy can have a cervical lateral mass length of about 12.4 mm and a cervical lateral mass width of about 12.8 mm for a sub-axial cervical spine at cervical level C6. In some examples, a male patient anatomy can have a cervical lateral mass length of about 9.8 mm and a cervical lateral mass width of about 11.8 mm for a sub-axial cervical spine at cervical level C7. In some examples, a female patient anatomy can have a cervical lateral mass length of about 11.0 mm and a cervical lateral mass width of about 10.0 mm for a sub-axial cervical spine at cervical level C3. In some examples, a female can have a cervical lateral mass length of about 11.5 mm and a cervical lateral mass width of about 10.3 mm for a sub-axial cervical spine at cervical level C4. In some examples, a female patient anatomy can have a cervical lateral mass length of about 11.4 mm and a cervical lateral mass width of about 11.0 mm for a sub-axial cervical spine at cervical level C5. In some examples, a female patient anatomy can have a cervical lateral mass length of about 11.1 mm and a cervical lateral mass width of about 11.1 mm for a sub-axial cervical spine at cervical level C6. In some examples, a female patient anatomy can have a cervical lateral mass length of about 8.5 mm and a cervical lateral mass width of about 10.3 mm for a sub-axial cervical spine at cervical level C7.

In some embodiments, one or more bone screws 12 of the kit or set of surgical system 10 are selected based on the examples of male and female cervical measurements described herein, and dimensions of length L and/or diameter D1 are selected having length L in a range of about 6.0 mm to about 9.0 mm and diameter D1 in a range of about 5.5 mm to about 7.0 mm. In some embodiments, one or more bone screws 12 of the kit or set of surgical system 10 are selected based on the examples of male and female cervical measurements described herein, and length L and/or diameter D1 are selected such that bone screw 12 includes a ratio L/D1 of about 2.0 or less, as shown by the table in FIG. 7. In some embodiments, length L and/or diameter D1 are selected such that bone screw 12 includes a ratio L/D1 of less than about 2.0.

Figure 4:
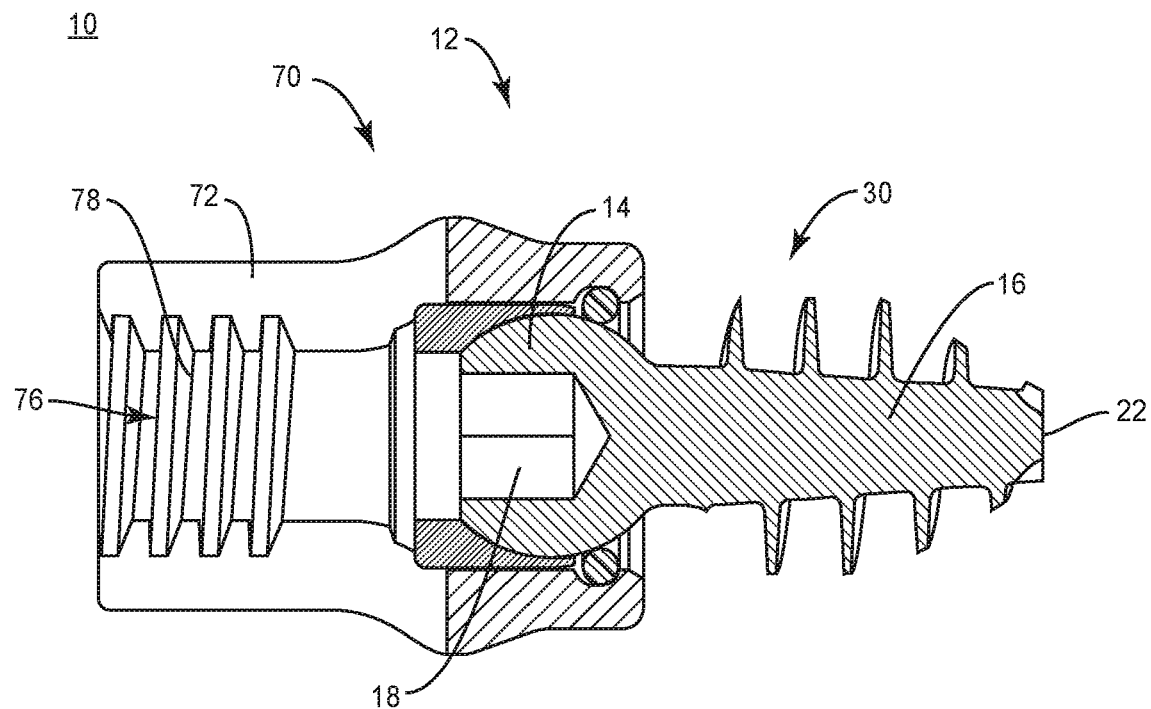
FIG. 4 is a cross section view of components of one embodiment of a system including a circular snap ring in accordance with the principles of the present disclosure.
Figure 5:
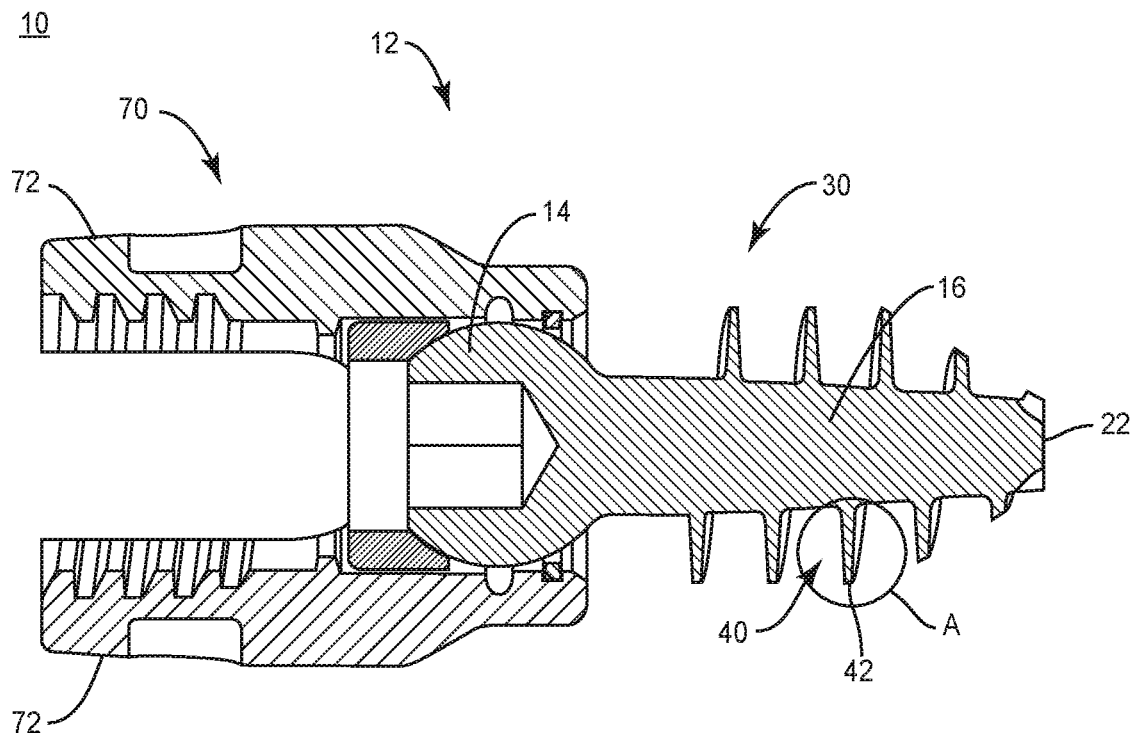
FIG. 5 is a cross section view of components of one embodiment of a system including a square snap ring in accordance with the principles of the present disclosure.

In some embodiments, head 14 is configured for connection with a receiver 70, as shown in FIGS. 4 and 5. Receiver 70 extends along axis X1. Receiver 70 includes a pair of spaced apart arms 72 that define an implant cavity 76 therebetween configured for disposal of a component of a spinal construct, such as, for example, a spinal rod (not shown). Arms 72 each extend parallel to axis X1. In some embodiments, arms 72 may be disposed at alternate orientations, relative to axis X1, such as, for example, transverse, perpendicular and/or other angular orientations such as acute or obtuse, coaxial and/or may be offset or staggered.

Cavity 76 is substantially U-shaped. In some embodiments, all or only a portion of cavity 76 may have alternate cross section configurations, such as, for example, closed, V-shaped, W-shaped, oval, oblong triangular, square, polygonal, irregular, uniform, non-uniform, offset, staggered, and/or tapered. Receiver 70 includes an inner surface 78 that includes a thread form. The thread form is configured for engagement with a coupling member, such as, for example, a setscrew (not shown), to retain a spinal construct, such as, for example, a spinal rod (not shown) within cavity 76. In some embodiments, surface 78 may be disposed with the coupling member in alternate fixation configurations, such as, for example, friction fit, pressure fit, locking protrusion/recess, locking keyway and/or adhesive. In some embodiments, all or only a portion of surface 78 may have alternate surface configurations to enhance engagement with the spinal rod and/or the setscrew such as, for example, rough, arcuate, undulating, mesh, porous, semi-porous, dimpled and/or textured. In some embodiments, receiver 50 may include alternate configurations, such as, for example, closed, open and/or side access.

In some embodiments, connection of head 14 with a receiver 70 forms various bone screw configurations, such as, for example, multi-axial screws, sagittal angulation screws, pedicle screws, mono-axial screws, uni-planar screws, fixed screws, anchors, tissue penetrating screws, conventional screws, expanding screws. In some embodiments, head 14 is configured for connection with a spinal implant, such as, for example, a plate. In some embodiments, head 14 is configured for connection with a post and/or connector that comprise a spinal construct and/or may be connected with a spinal rod. In some embodiments, head 14 may include and/or be integrally connected or monolithically formed with a post, and/or the post may be rotatable relative to axis X1.

In assembly, operation and use, surgical system 10, similar to the systems and methods described herein, includes a selected bone screw 12 and is employed with a surgical procedure for treatment of a condition or injury of an affected section of the spine. Surgical system 10 is utilized for treatment of a condition or injury of an affected section of the spine including cervical vertebrae V, such as, for example, lateral mass tissue LM of a cervical spine. In one embodiment, as shown in FIGS. 9-11, the components of surgical system 10 are employed with a method to treat vertebrae V.

In use, to treat a selected section of vertebrae V, a medical practitioner obtains access to a surgical site including vertebrae V, such as, for example, along a surgical pathway P. In some embodiments, surgical pathway P is oriented at angle α relative to vertebrae V. In some embodiments, surgical system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway, which includes surgical pathway P, in alignment with a surgical approach, as described herein, for implantation of components of surgical system 10. A preparation instrument (not shown) can be employed to prepare tissue surfaces of vertebrae V, as well as for aspiration and irrigation of a surgical region.

Bone screw 12 is selected having a length L and a diameter D based on a cervical level of vertebrae V and patient criteria, such as, for example, male, female, lateral mass length LML and/or lateral width LMW. For example, lateral mass length LML and lateral width LMW of the patient is determined and diameter D1 and length L of bone screw 12 is selected from one or more bone screws 12 of the kit or set of surgical system 10. In some embodiments, diameter D1 and length L are selected based on the patient criteria and bone screw 12 is selected having a ratio L/D1 about 2.0 or less to resist and/or prevent damage to vertebral arteries and/or nerves. In some embodiments, diameter D1 and length L are selected based on the patient criteria and bone screw 12 is selected having a ratio L/D1 less than about 2.0 to resist and/or prevent damage to vertebral arteries and/or nerves.

Head 14 is engaged with a surgical instrument, such as, for example, a driver (not shown). In some embodiments, bone screw 12 is connected with a receiver 70 (FIGS. 4 and 5). Bone screw 12 is translated such that axis X1 of shaft 16 is disposed along surgical pathway P. Surgical pathway P includes a trajectory disposed at angle α to penetrate lateral mass tissue LM. In some embodiments, angle α is in a range of about 0 through about 10 degrees. The driver is rotated causing bone screw 12 to translate axially within a pilot hole. Shaft 16 translates such that thread 30 engages lateral mass tissue LM and avoids penetrating the anterior cortex of lateral mass LM.

As bone screw 12 is translated into lateral mass tissue LM, thread 30 engages lateral mass tissue LM. Thread 30 disrupts, scrapes, cuts and/or removes tissue and guides the cut tissue into cavity S. Manipulation of bone screw 12, including rotation and/or translation, causes edges 50, 52 to disrupt, scrape, cut and/or remove tissue at a surgical site and guide the cut tissue into cavity S. Such tissue can become imbedded into cavity S to promote bone growth to enhance fusion of bone screw 12 and increase resistance and pull out force of bone screw 12, as described herein. In some embodiments, dimensions of bone screw 12, as described herein, can be configured to facilitate thread 30 cutting and/or slicing through bone like a narrow wedge. In some embodiments, the dimensions of bone screw 12 are configured to minimize an impact to the microstructure of tissue.

In some embodiments, length L of bone screw 12 resists and/or prevents damage to vertebral arteries and/or nerves and diameter D1 resists and/or prevents pullout while maintaining structural integrity. Upon engagement of bone screw 12 with lateral mass LM, height H1, width W1 and width W2 allow lateral mass LM to contract against surfaces of thread 30 creating friction and providing tactile feedback to a practitioner to indicate proper engagement and placement of bone screw 12.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of rods, plates, connectors and/or bone fasteners for use with a single vertebral level or a plurality of vertebral levels.

In some embodiments, one or more bone fasteners, such as, for example, bone screw 12 may be engaged with tissue in various orientations, such as, for example, series, parallel, offset, staggered and/or alternate vertebral levels. In some embodiments, one or more bone spinal implants may comprise multi-axial screws, sagittal angulation screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone screw comprising:
    a receiver including a body, the body comprising an inner surface defining an aperture, a proximal opening and a distal opening, the openings being in communication with the aperture, the receiver including a pair of spaced apart arms extending from the body, the arms defining an implant cavity therebetween, the proximal opening being positioned between the implant cavity and the aperture;
    a crown positioned in the aperture, the crown having a width greater than a width of the proximal opening;
    a first portion including a head; and
    a second portion connected to the first portion and including a threaded shaft having a length and a major diameter, the shaft including a length-to-major diameter ratio of less than 2.0, the head being positioned within the aperture such that the second portion is rotatable relative to the receiver, the thread having a minor diameter and includes a major-diameter-to-minor diameter ratio of greater than 2.0, the shaft further having at least one thread including a pitch of greater than 1.0 mm and defining a pitch cavity for disposal of tissue, the at least one thread including a thread form having a thread depth and a base, the thread form including a thread-depth-to-base ratio of 5.0.

2. A bone screw as recited in claim 1, the thread form includes a leading surface of a flank and a trailing surface of an adjacent flank, the leading surface and the trailing surface defining the pitch cavity therebetween.

3. A bone screw as recited in claim 1, wherein the pitch is 1.5 mm.

4. A bone screw as recited in claim 1, wherein the thread form includes a thread form includes a tip having a width of 0.15 mm.

5. A bone screw as recited in claim 1, wherein the thread form includes a tip having a width in the range of 0.075 mm through 0.400 mm.

6. A bone screw as recited in claim 1, wherein the thread depth is in a range of 0.75 through 3.50 mm.

7. A bone screw as recited in claim 1, wherein the thread depth is 1.3 mm.

8. A bone screw as recited in claim 1, wherein the thread form has a leading edge angle in the range of −4.0 degree to 15 degrees.

9. A bone screw as recited in claim 1, wherein the thread form has a leading edge angle of 5 degrees.

10. A bone screw as recited in claim 1, wherein the thread form has a trailing edge angle in the range of −4.0 degrees to 15 degrees.

11. A bone screw as recited in claim 1, wherein the thread form has a thread form having a trailing edge angle of 5 degrees.

12. A bone screw as recited in claim 1, wherein the head is non-threaded and includes a spherical portion.

13. A bone screw as recited in claim 1, wherein the second portion extends along a longitudinal axis between opposite proximal and distal end surfaces, the proximal end surface directly engaging the first portion, the distal end surface being planar and extending perpendicular to the longitudinal axis.

14. A bone screw comprising:
    a receiver including a body, the body comprising an inner surface defining an aperture, a proximal opening and a distal opening, the openings being in communication with the aperture, the receiver including a pair of spaced apart arms extending from the body along a longitudinal axis, the arms defining an implant cavity therebetween, the proximal opening being positioned between the implant cavity and the aperture along the longitudinal axis;
    a crown positioned in the aperture such that a proximal end of the crown extends into the implant cavity, the crown having a width greater than a width of the proximal opening;
    a first portion including a head; and
    a second portion connected to the first portion and including a threaded shaft having a length and a major diameter, the shaft including a length-to-major diameter ratio of less than 2.0, the head being positioned within the aperture such that the second portion is rotatable relative to the receiver, the thread having a minor diameter including a major-diameter-to-minor-diameter ratio of greater than 2.0, the shaft further having at least one thread including a pitch of greater than about 1.0 mm, a thread depth, a base and a tip, wherein the pitch is 1.5 mm, wherein a thread-depth-to-base ratio is 5, and the at least one thread includes a leading surface of a flank and a trailing surface of an adjacent flank, the leading surface and the trailing surface defining a pitch cavity therebetween.

15. A bone screw as recited in claim 14, wherein the cavity includes a configuration defined by the pitch and the thread depth of the at least one thread.

16. A bone screw as recited in claim 14, wherein the pitch is 1.5 mm.

17. A bone screw comprising:

a receiver including a body, the body comprising an inner surface defining an aperture, a proximal opening and a distal opening, the openings being in communication with the aperture, the receiver including a pair of spaced apart arms extending from the body along a longitudinal axis, the arms defining an implant cavity therebetween, the receiver including a flange that defines the proximal opening, the implant cavity being configured for disposal of a spinal rod, the proximal opening being positioned between the implant cavity and the aperture along the longitudinal axis, the aperture and the implant cavity each having a maximum width that is greater than a maximum width of the proximal opening;

a crown positioned in the aperture such that a proximal end of the crown directly engages a distal surface of the flange, the crown having a maximum width that is greater than the maximum width of the proximal opening, the inner surface including only one groove between a distal end of the crown and the distal opening;

a first portion including a head, the head being non-threaded and including a spherical portion;

a ring positioned in the groove such that the ring engages the head; and a second portion extending along a longitudinal axis between opposite proximal and distal end surfaces, the proximal end surface directly engaging the first portion, the distal end surface being planar and extending perpendicular to the longitudinal axis, the second portion including a threaded shaft having a length and a major diameter, the shaft including a length-to-major diameter ratio of less than 2.0, the head being positioned within the aperture such that the second portion is rotatable relative to the receiver, the second portion being non-cannulated, the thread having a minor diameter and includes a major-diameter-to-minor diameter ratio of greater than 2.0, the shaft further having at least one thread including a pitch of greater than about 1.0 mm and defining a pitch cavity for disposal of tissue, wherein the pitch is 1.5 mm, wherein the at least one thread includes a thread form having a thread depth and a base, the thread form including a thread-depth-to-base ratio of 5.0, wherein the at least one thread includes a tip having a width in the range of 0.075 mm through 0.400 mm, wherein the thread form includes a thread depth in a range of 0.75 through 3.50 mm, wherein the thread form has a leading edge angle in the range of −4.0 degrees to 15 degrees, and wherein the thread form has a trailing edge angle in the range of −4.0 degrees to 15 degrees.

* * * * *